US011272880B2

(12) United States Patent
Wallois et al.

(10) Patent No.: US 11,272,880 B2
(45) Date of Patent: Mar. 15, 2022

(54) DEVICE FOR MEASURING THE BRAIN ACTIVITY SIGNALS OF AN INDIVIDUAL

(71) Applicants: CENTRE HOSPITALIER UNIVERSITAIRE, Amiens (FR); UNIVERSITE AMIENS PICARDIE JULES VERNE, Amiens (FR); INSERM (INSTITUT NATIONAL DE LA SANTE ET DE LA RECHERCHE MEDICALE), Paris (FR); ETABLISSEMENTS MALTERRE SARL, Moreuil (FR)

(72) Inventors: Fabrice Wallois, Amiens (FR); Mahdi Mahmoudzadeh, Amiens (FR); Reinhard Grebe, Hebecourt (FR); Laurent Malterre, Moreuil (FR); Javad Safaie, Amiens (FR)

(73) Assignees: CENTRE HOSPITALIER UNIVERSITAIRE, Amiens (FR); UNIVERSITE AMIENS PICARDIE JULES VERNE, Amiens (FR); INSERM (INSTITUT NATIONAL DE LA SANTÉ ET DE LA RECHERCHE MÉDICALE), Paris (FR); ETABLISSEMENTS MALTERRE SARL, Moreuil (FR)

( * ) Notice: Subject to any disclaimer, the term of this patent is extended or adjusted under 35 U.S.C. 154(b) by 1336 days.

(21) Appl. No.: 15/528,222

(22) PCT Filed: Nov. 19, 2015

(86) PCT No.: PCT/FR2015/053132
§ 371 (c)(1),
(2) Date: May 19, 2017

(87) PCT Pub. No.: WO2016/079436
PCT Pub. Date: May 26, 2016

(65) Prior Publication Data
US 2017/0367650 A1 Dec. 28, 2017

(30) Foreign Application Priority Data

Nov. 21, 2014 (FR) .................................. 14 61283

(51) Int. Cl.
*A61B 5/04* (2006.01)
*A61B 5/00* (2006.01)
(Continued)

(52) U.S. Cl.
CPC .......... *A61B 5/6803* (2013.01); *A61B 5/0075* (2013.01); *A61B 5/0261* (2013.01);
(Continued)

(58) Field of Classification Search
CPC ........... A61B 5/291; A61B 5/369; A61B 5/24; A61B 5/4094; A61B 5/282; A61B 5/6814;
(Continued)

(56) References Cited

U.S. PATENT DOCUMENTS 3,998,213 A    12/1976   Price
5,800,351 A *   9/1998   Mann ..................... A61B 5/291
                                                                600/383
(Continued)

FOREIGN PATENT DOCUMENTS

EP    0 541 393 A1    5/1993
FR    2 627 975 A1    9/1989
(Continued)

OTHER PUBLICATIONS

European Office Action for Application No. 15 804 902.3, dated Sep. 21, 2018.
(Continued)

*Primary Examiner* — Joseph A Stoklosa
*Assistant Examiner* — Brian M Antiskay (74) *Attorney, Agent, or Firm* — Nixon & Vanderhye (57) ABSTRACT

Disclosed is a device suitable for measuring the brain activity signals of an individual, the device being intended to be placed on the head of the individual and having a structure intended to carry sensors, the structure allowing the position of the sensors to be adjusted. The structure of the device has: a deformable central support, which is able to adapt to the curvature of the head and is intended to be positioned along the head, preferably on the median plane of the cranium; flexible guides, which extend laterally with respect to the central support and are spaced apart from each other; sensor supports, which are rigidly connected and fixed to the flexible guides, in adjustable positions along the flexible guides; and a system for tightening the flexible guides.

22 Claims, 5 Drawing Sheets

(51) Int. Cl.
| | | |
|---|---|---|
| *G06F 3/01* | (2006.01) | |
| *A61B 5/1455* | (2006.01) | |
| *A61B 5/026* | (2006.01) | |
| *A61B 5/291* | (2021.01) | |

(52) U.S. Cl.
CPC .......... *A61B 5/14553* (2013.01); *A61B 5/291* (2021.01); *G06F 3/015* (2013.01); *A61B 5/6843* (2013.01); *A61B 2562/0238* (2013.01)

(58) Field of Classification Search
CPC ....... A61B 5/0006; A61B 5/25; A61B 5/6803; A61N 1/0456; A61N 1/0529; A61N 1/0484; A61N 1/0476; A61N 1/36064; A61N 1/0526
USPC ........ 600/372, 382–384, 386, 388–390, 393, 600/544–545; 607/115, 139
See application file for complete search history.

(56) References Cited

U.S. PATENT DOCUMENTS

| | | | |
|---|---|---|---|
| 6,161,030 A * | 12/2000 | Levendowski | A61B 5/6804 600/383 |
| 8,019,402 B1 | 9/2011 | Kryzpow et al. | |
| 10,500,424 B2 * | 12/2019 | Rummery | A61M 16/0622 |
| 2001/0044573 A1 * | 11/2001 | Manoli | A61B 5/6804 600/383 |
| 2005/0107716 A1 | 5/2005 | Eaton et al. | |
| 2008/0294031 A1 * | 11/2008 | Wilson | A61B 5/296 600/383 |
| 2009/0088619 A1 | 4/2009 | Turner et al. | |
| 2009/0247839 A1 | 10/2009 | Ninomiya et al. | |
| 2010/0274153 A1 | 10/2010 | Tucker et al. | |
| 2011/0098593 A1 * | 4/2011 | Low | A61B 5/369 600/544 |
| 2011/0152659 A1 * | 6/2011 | Chen | A61B 5/291 600/372 |
| 2011/0319975 A1 * | 12/2011 | Ho | A61N 1/0456 607/139 |
| 2012/0173020 A1 * | 7/2012 | Seth | G06N 3/004 700/249 |
| 2014/0276183 A1 | 9/2014 | Badower | |
| 2015/0282760 A1 * | 10/2015 | Badower | A61B 5/291 600/383 |

FOREIGN PATENT DOCUMENTS

| | | | |
|---|---|---|---|
| FR | 2 899 089 A1 | | 10/2007 |
| JP | H07-27504 U | | 5/1995 |
| JP | 2009-131643 A | | 6/2009 |
| JP | 2009-240454 A | | 10/2009 |
| JP | 2011120866 A | * | 6/2011 |
| JP | 2014-036862 A | | 2/2014 |
| WO | 99/22642 A1 | | 5/1999 |
| WO | 2012/156643 A1 | | 11/2012 |
| WO | 2014/169241 A1 | | 10/2014 |

OTHER PUBLICATIONS

Office Action issued in Japanese Patent Application No. 2047-546049 dated Oct. 7, 2019 with English translation provided.
NR Sign Inc., "EEG Cap", http://www.nrsign.com/eeg-cap/.
International Search Report, dated Jan. 29, 2016, from corresponding PCT application.

* cited by examiner

DEVICE FOR MEASURING THE BRAIN ACTIVITY SIGNALS OF AN INDIVIDUAL

BACKGROUND OF THE INVENTION

Field of the Invention

The present invention relates to a device for measuring brain activity signals, suitable for being positioned on the head of an individual.

The device can be used, in particular, both for measuring electrical brain activity by electroencephalography and for measuring data relating to the hydrodynamic conditions of the circulation in the brain, such as tissue oxygenation, by near-infrared spectroscopy.

Description of the Related Art

Electroencephalography devices comprising electrodes are known, which enable the acquisition of an electroencephalogram, i.e. recording electrical brain activity in the form of a signal. Said devices use sensors consisting of electrical electrodes which are arranged on the head of individuals to be diagnosed or investigated using headsets or caps, usually referred to as "electroencephalography headsets" (or EEG headsets) Such caps made from fabric have being marketed under the trademark "Easycap".

The fabric headsets have the disadvantage of not being able to easily manipulate the hair of the individual, which disturbs the acquisition of signals for near-infrared spectroscopy. Indeed, hair must be excluded from the field of measurement.

In addition, near-infrared spectroscopy (NIRS) at wavelengths between 600 and 900 nm can report haemodynamic brain activity in the form of a signal, the sensors used being detectors (optical fibres, photodiodes) or transmitters (optical fibres, LEDs) of optical photons, that are also known as "optodes".

Often, these devices are equipped with electrodes only, and are designed only to produce an electroencephalogram, or alternatively are equipped with optical transmitters and detectors and are designed to produce a near-infrared spectroscopy. In other words, these dedicated devices do not allow simultaneous measurement of signals by electroencephalography and by near-infrared spectroscopy.

The fabric headsets designed for electrodes are too flexible to allow correct arrangement of the optodes with respect to the surface of the head, the supports thereof being too heavy and thus causing deformation of the fabric. These fabric headsets, being too weak, are unable to hold an arrangement of optodes strictly perpendicular to the cranium of the individual throughout the duration of the recording. Moreover, such flexible headsets do not allow a precise spatial resolution or a reliable measurement of the electrical and haemodynamic activities originating in the brain to be obtained.

However, the prior art of FR 2 899 089 contains a signal sensor device comprising an electrode and an optode arranged on the same support, concentrically with respect to an axis intended to be substantially perpendicular to the head. Such a device advantageously allows precise targeting of a given area of interest on the head of the individual, and in such a way as to allow simultaneous measurement of signals by electroencephalography and by near-infrared spectroscopy. Such an EEG/NIRS sensor device however has the disadvantage of a non-competitive cost price when compared to two structurally independent sensors, being respectively an electrode and an optode.

More rigid headsets are known which combine the wearing of electrodes and optodes, termed modular headsets, such as those marketed under the trademark Shimadzu®. These relatively rigid, plastic material headsets are made from polypropylene and cover the entire head, while being provided with a plurality of distinct holes depending on the type of sensor to be received.

However, the arrangement of devices described above on the head of a person is unsatisfactory in terms of the quality of the contacts of the electrical and optical devices, due to the curvature of the head, the presence of the hair and a lack of flexibility of the device, in particular for young children and newborns. Furthermore, structures are known which are not caps and which comprise latex or rubber bands or straps which link together the nodes forming the supports for sensors or electrodes. The structure is thus produced in the form of a network provided with recesses for passage of the hair. For example, patent applications FR 2 627 975, US 2010/274153, EP 0 541 393 and WO 99/22642 can be cited.

However, the locations of the nodes are pre-established and do not always allow appropriate positioning of the sensors and electrodes for the head of the individual. In addition, for some structures, elastic straps promote sweating and can give rise to too large an application pressure on the head, in particular for an infant.

Also known is an "EEG" headset from NR Sign Inc. (http://www.nrsign.com/eeg-cap/) for which the headset structure comprises two braces connected by a chinstrap. The two braces are intended to be arranged on either side of the head respectively, at least locally below the ears. A set of silicone elastic threads, links the two braces by passing over the head, the threads extending laterally to the head and spaced apart from one another. Once tensioned between the two braces, each silicone thread is able to hold an electrode support, elastically squeezed between the head of the individual and the silicone thread, the silicone thread thus simply bearing on the electrode support.

Such a device has the advantage of allowing accurate (continuous) adjustment of the electrode support along the silicone thread.

On the other hand, and according to the findings of the inventors, such a headset has major disadvantages, and in particular:
  the design and footprint of the sensor supports only allows a small number of EEG electrodes to be positioned on the head of an individual; under no circumstances does such a device allow simultaneous positioning of structurally independent electrode sensors and optode sensors, at a concentration allowing targeting of the same areas of interest,
  the placing of such a headset, in particular adjustment of the positions of the sensor supports along the silicone threads, must compulsorily be carried out directly on the head of the individual: in other words it is not possible to prearrange the sensor supports on the head of a mannequin in that, once the headset is removed from the mannequin, the position settings are lost.

A device for measuring brain activity signals is also known from WO2012/156643, which is intended to be affixed on the head of an individual and enables simultaneous measurement of signals by electroencephalography and by near-infrared spectroscopy, the device having both parts for receiving electrodes as well as other parts for receiving optical detectors and transmitters (optodes).

The structure of said device comprises a central chain and side chains, each resulting from the assembly of constituent links which can be articulated with respect to one another. Some of the links comprise parts suitable for supporting electrodes, other links comprising parts for supporting optodes.

According to the findings of the inventors, such a device structure has the following disadvantages:
- the (central or side) chains, resulting from the assembly of rigid links, cause pain to the individual, in that the chains press on the head at a plurality of "hard" contacts,
- such a link structure clearly enables adjustment of the position of the sensors (electrodes or optodes) in different possible mounting positions on the links. However, this only involves setting the position in several discrete pre-established positions, defined by the links, and does not provide the possibility of continuous adjustment along the chains,
- according to the findings of the inventors, the concentration of different sensors can still be improved.

BRIEF SUMMARY OF THE INVENTION

The problem addressed by the present invention is that of overcoming the above-mentioned disadvantages, by proposing a device for measuring brain activity signals, the structure of which allows, at least according to the particular embodiments:
- access to the scalp in a such a way as to disengage the hair from the sensors, in particular optode transmitters/detectors, and/or electrodes,
- wearing comfort for the user, without creating too large a pressure giving rise to pain,
- adjustment of the position of various sensor supports, in different positions, and preferably continuously along the lateral guides,
- carrying out installation of the device, including performing pre-adjustments of the positions of the various sensor supports on the head of a mannequin, then withdrawing the device thus prepared in order to place it on the head of an individual, advantageously without loss of the position settings,
- wearing of a large number of sensors, in particular electrodes and optodes, with a spatial density allowing simultaneous acquisition of signals by electroencephalography and by near-infrared spectroscopy, over the targeted areas of interest.

The invention also relates to a device for measuring the brain activity signals of an individual, said device being intended to be placed on the head of said individual and having a structure intended to carry sensors, said structure allowing the position of the sensors to be adjusted.

According to the invention, said structure of the device comprises:
- a central support, preferably deformable, which is able to adapt to the curvature of the head and is intended to be positioned along the head, preferably on the median plane of the cranium;
- flexible guides, extending laterally with respect to said central support and spaced apart from each other;
- sensor supports, which are rigidly connected and fixed to said flexible guides, in adjustable positions along the flexible guides;
- and a system for tensioning said flexible guides.

According to the optional features of the invention, taken alone or in combination:
- said system for tensioning the flexible guides, comprises, on each side of the head of the wearer, a rigid brace, intended to extend at least locally under the ear, the two braces being preferably connected by a chinstrap, and elastic pieces, each rigidly attached by the one of the ends thereof to the lower terminal end below of the corresponding flexible guide, each elastic piece being intended to be attached to said brace in order to ensure the tensioning of the corresponding flexible guide;
- said tensioning system comprises a means for adjusting the tension of the elastic piece.
- the means for adjusting the tension of the elastic piece comprises a through-opening of the brace for the elastic piece, said through-opening having dimensions less than the cross-section of the elastic piece, such that:
  a manual pulling force on the free end of the elastic piece causes the elastic piece to slide through said through-opening, and thus enables adjustment by increasing the tension, and when the manual force is no longer applied,
  the frictional forces between the through-opening and the elastic piece are such as to prevent sliding, ensuring the tensioning of the corresponding flexible guide;
- the flexible guides are made from an inelastic material;
- the flexible guides are made from a textile;
- the flexible guides are bands;
- said sensor supports are in adjustable positions along the flexible guides, said sensor supports having feedthroughs for the flexible guides allowing such a position adjustment;
- once the manual adjustment operation has been carried out, the sensor support is held in position on the flexible guide by the frictional forces between the flexible guide and the sensor support;
- said sensor supports each comprise a portion having a foot, made in particular from elastomer, intended to bear on the head of the wearer;
- said portion of the sensor support having the support foot comprises two so-called feedthroughs, positioned respectively on either side of said foot, both crossed by one of the flexible guides, as well as a dorsal surface on which the longitudinal section of said flexible guide bears at a position intermediate between the two feedthroughs;
- all or part of the sensor supports are so-called multiple sensor supports, each able to support at least two physically distinct sensors;
- said so-called multiple sensor supports comprise sensor supports for two sensors intended to be positioned either side of said support foot;
- said so-called multiple sensor supports comprise sensor supports for four sensors, intended to be distributed around said support foot;
- each sensor is intended to be moveably mounted, by sliding, with respect to the portion of the sensor support equipped with the support foot; a spring element, such as a compression spring, being configured to constrain the sensor in the direction towards and pressing on the head of the individual;
- said sensor support portion equipped with said support foot being termed the fixed part, said sensor support comprises, for the or each sensor, a moveable part movable with respect to said fixed part, on which the sensor is rigidly attached, said spring element being provided between the fixed part and the moveable part of the sensor support;

said fixed part comprises, for the or each sensor, a hollow shaping, in particular cylindrical, inside of which the movable part is intended to slide, and in which said movable part of the sensor support has a terminal end for attaching a sensor, as well as a guide surface intended to slide along the inner wall of the hollow shaping;

said movable part has a projecting portion extending through an upper opening of the hollow shaping, a locking member, such as a pin, being mounted in a removable manner on the projecting portion, in such a way as to both ensure the holding and locking of said moveable part to said fixed part of the sensor support, as well as to enable, once the locking member is withdrawn, the withdrawal and dismantling of the moveable part from the fixed part;

the locking member takes the shape of a loop, intended for gripping, and allowing the sensor to be removed from the surface of the head when a traction force is applied on the loop;

said central support has, in the longitudinal direction, a plurality of through-passages, mutually spaced along the length of said central support for the respective positioning and holding of a plurality of flexible guides, having different separated positions defined between said flexible guides;

said central support forms, along the longitudinal direction, a longitudinal channel acting as a cable guide, intended for guiding the wiring connections of the various sensors;

the device comprises an enclosure accommodating acquisition electronics for the sensor signals;

the device has sensors comprising electrodes for measuring signals by electroencephalography and/or optical detectors and transmitters for measuring signals by near-infrared spectroscopy.

the device comprises a removable cover, made from an obscuring material, intended to be applied on the sensor support structure of the device in such a way as to isolate the sensors from optical interference from the ambient environment.

The invention also relates to use of a device according to the invention equipped with sensors comprising said electrodes for measuring signals by electroencephalography and said optical detectors and transmitters for measuring signals by near-infrared spectroscopy, for simultaneously measuring said signals by electroencephalography and near-infrared spectroscopy.

BRIEF DESCRIPTION OF THE DRAWINGS

The invention will be better understood on reading the following description together with the attached drawings, of which.

DETAILED DESCRIPTION OF THE PREFERRED EMBODIMENTS

Figure 1:
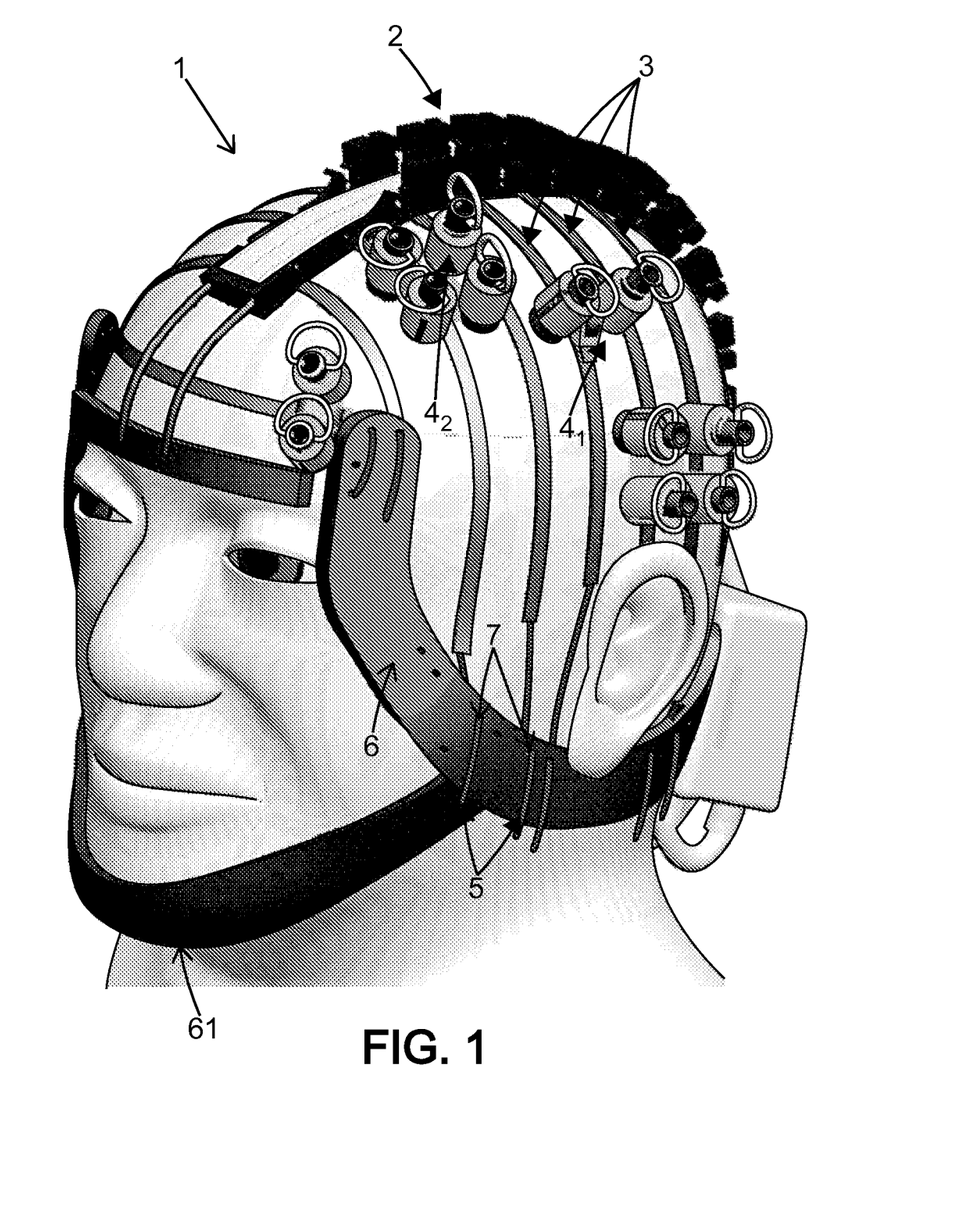
FIG. 1 is a perspective view of a device according to the invention, placed on the head of an individual.

The invention relates to a device 1 for measuring the brain activity signals of an individual, said device being intended to be placed on the head of said individual and having a support structure intended to carry sensors, said structure allowing the position of the sensors to be adjusted.

According to the invention, said structure of the device comprises:

a, preferably deformable, central support 2, which is able to adapt to the curvature of the head and is intended to be positioned along the head, preferably on the median plane of the cranium;

flexible guides 3, extending laterally to said central support, in particular on either side of said central support, spaced apart from one another, sensor supports $4_1$, $4_2$, attached and rigidly connected to said flexible guides, in adjustable positions along the guides;

and a system 5, 6 for tensioning said flexible guides 3.

The flexible guides 3 are distributed over the surface of the head, mutually spaced apart from each other, according to predefined spacings, in particular by said central support 2. During installation this structure makes it possible to access the scalp and thus to disengage the hair from the sensors positioned by the sensor supports at different spacings between the flexible guides.

The sensor support(s) $4_1$, $4_2$ are attached and rigidly connected to said flexible guides 3, but at adjustable positions along said guides. This possibility to adjust the position makes it possible, in particular, to adapt the positions of the various sensors depending on the areas of interest to be studied.

The fact that the sensor supports $4_1$, $4_2$ are rigidly attached to the flexible guides 3, and not simply bearing against same, advantageously makes it possible to carry out a pre-assembly of the structure, including a pre-adjustment of the positions of the various sensors on the head of a mannequin, and then to remove the structure and affix it on the head of the individual, advantageously without loss of the position settings along the flexible guides 3.

Said system for tensioning the flexible guides, may comprise, on each side of the head of the wearer, a rigid or semi-rigid brace 6, intended to extend at least locally under the ear, the two braces 6 being preferably connected by a chinstrap 61, and elastic pieces 5, each rigidly attached by one of the ends thereof to the lower terminal end of the corresponding flexible guide 3, each elastic piece 5 being intended to be attached to said brace 6 in order to ensure the tensioning of the corresponding flexible guide 3;

It should be noted that according to this advantageous embodiment, the flexible guides 3 and corresponding elastic pieces 5 are distinct elements; thus, for the flexible guides, it is possible to choose a material (for example a conventional textile) that is inelastic in comparison to the material of the elastic pieces 5 which can be made of silicone or another elastomer-type material.

According to the findings of the inventors, the choice of an inelastic material for the flexible guides 3 (compared to the material of the elastic pieces 5), makes it advantageously possible to ensure, during a pre-adjustment of the structure on the head of a mannequin, that the sensors are positioned in substantially the same positions once the structure is withdrawn from the mannequin and placed on the head of the individual, without any offset of the positioning as would be encountered in the case where the flexible guides were made from the same material as the elastic pieces 5.

In particular, in the case where the sensor supports $4_1$, $4_2$ are fixed to the flexible guides by means of feedthroughs 40, 41; 42, 44; 43, 45 of the supports, through which the flexible guides 3 pass, and which are described below, the fact of choosing flexible guides made from an inelastic (or inextensible) material makes it possible to avoid, or at least limit, the phenomena of reducing of the cross-section of the flexible guides when same are tensioned; reducing the cross-section in the case where the flexible guides were made from an elastic material, would cause a loss of position of the sensor supports along the flexible guides.

According to one embodiment, the flexible guides 3 and the sensor supports $4_1$, $4_2$ are arranged such that the flexible guides 3 press on the head of said individual, completely or partially, at sections of the length of the flexible guide 3, at intermediate positions between the sensor supports $4_1$, $4_2$. In order to stabilise the pressing of the flexible guide 3 and to ensure a uniform distribution, each flexible guide can take the shape of a band, intended to press on the head by means of one of the faces thereof.

According to one embodiment, said tensioning system comprises a means for adjusting the tension of the elastic piece. For example, and as illustrated in a non-limiting manner in FIG. 1, the means for adjusting the tension of the elastic piece (of each elastic piece 5) comprises a through-opening 7 of the brace for the elastic piece 5, said through-opening 7 having dimensions less than the cross-section of the elastic piece 5, such that:
- a manual pulling force on the free end of the elastic piece 5 causes the elastic piece to slide through said through-opening 7, and thus enables adjustment by increasing the tension, and when the manual force is no longer applied,
- the frictional forces between the through-opening 7 and the elastic piece 5 are such as to prevent sliding, ensuring the tensioning of the corresponding flexible guide.

Such a tensioning system also allows an adjustment of the tension of each flexible guide 3 by tensioning said corresponding elastic piece, allowing all of the sensors supports to be constrained on the head by said flexible guide. This advantageously involves the possibility of continuous adjustment. Other embodiments of tension adjustment means are possible, in particular non-continuous adjustment types, for example by providing several hooking positions for the elastic piece (not shown) on the brace in order to allow different tension forces.

Figure 13:
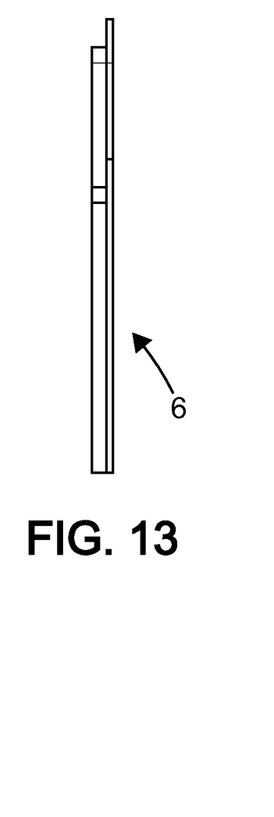
FIGS. 13 and 14 are a side view and front view of the (right-hand) brace of the device.
Figure 14:
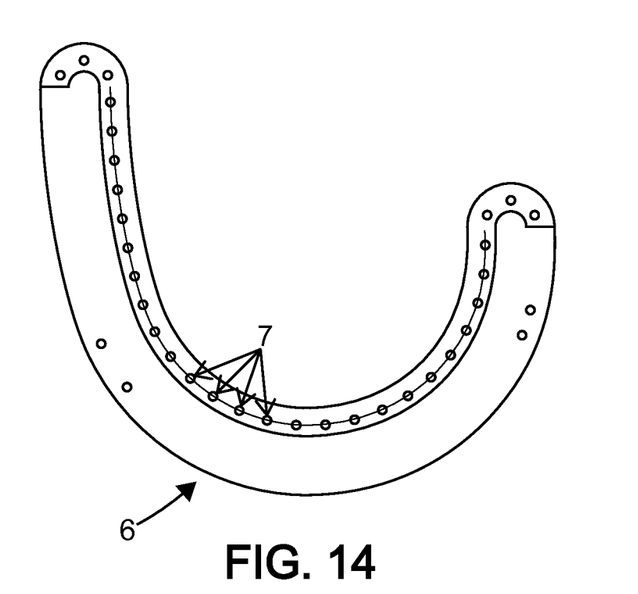

The brace may be an element made from curved plastic, as illustrated in FIGS. 13 and 14, intended to extend, for example, from the rear part of the head, passing under the ear and continuing to a lateral area in the vicinity of the forehead. Along the length thereof, a plurality of through-openings 7 allows the insertion of elastic pieces 5 in the most suitable positions for the adjustment. On the inner face, and bearing on the skin, this element can be covered by a flexible material.

The possibility of adjusting the sensor supports 41, 42 along the guides can be provided by feedthroughs 40, 41; 42, 43, 44, 45 for the flexible guides, allowing such a position adjustment. The position adjustment is advantageously carried out without withdrawing the sensor support from the flexible guide thereof, by allowing same to slide manually along the flexible guide 3. Once this manual operation has been performed, i.e. the position of said sensor support has been adjusted, maintaining the position of the sensor support on the flexible guide 3 is advantageously ensured (uniquely) by the frictional forces between the flexible guide and the sensor support 41, 42.

According to one embodiment, said sensor supports 41, 42 each comprise a portion having a foot 46, intended to bear on the head of the wearer; In the case of a multiple-sensor support (supporting a plurality of physically distinct sensors), said support foot 46 is preferably in a central position with respect to the positions of the various supported sensors. Said foot can advantageously be made of a flexible material, different from the support body, for example an elastomer.

According to one embodiment, said portion of the sensor support having the support foot 46 can comprise two so-called feedthroughs 40, 41; 42, 44; 43, 45, positioned on the sensor support, respectively on either side of said foot 46, both passed through by one of the flexible guides 3, as well as a dorsal surface 47 on which longitudinal section of said flexible guide presses at a position intermediate between the two feedthroughs 40, 41; 42, 44; 43, 45.

Figure 2:
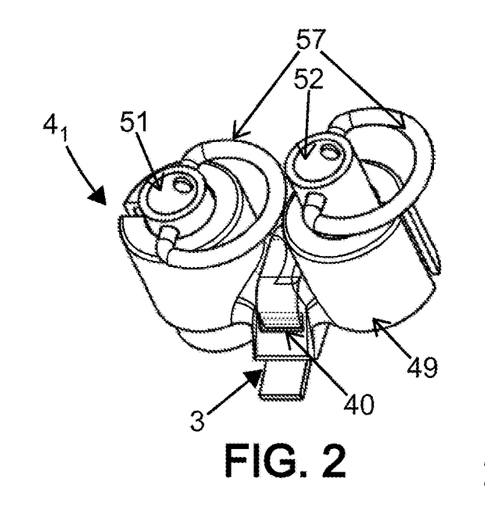
FIGS. 2, 3 and 4 are respectively a perspective view, a view from above, and a sectional view along section III-III of FIG. 3, of a sensor support having two sensors.
Figure 3:
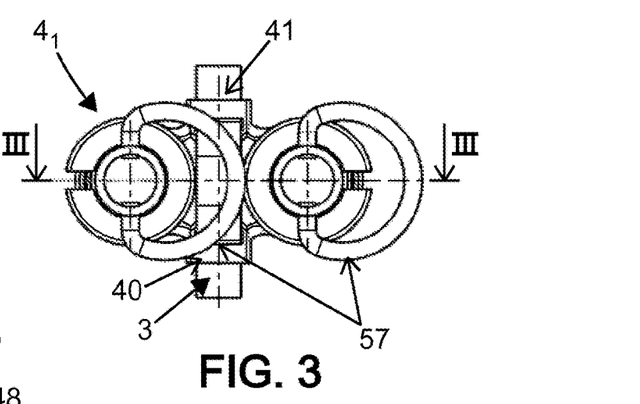

According to this embodiment, illustrated in a non-limiting manner, particularly in FIGS. 2 and 3, the flexible guide 3, in particular the band, passes through a first feedthrough 40 from underneath the support $4_1$, extends bearing along the dorsal surface 47, then passes through a second feedthrough 41 from above the support. It should be noted that the dorsal surface 47 can advantageously be positioned just above the foot 46, in order to increase stability (against tilting) of the sensor support $4_1$, $4_2$.

Advantageously, all or part of the sensor supports are so-called multiple sensor supports $4_1$, $4_2$, each able to support at least two physically distinct sensors. The presence of such multiple sensor supports advantageously allows an increase in the density of the positions of sensors over an area of interest.

Said so-called multiple sensor supports can comprise sensor supports $4_1$, for two sensors, intended to be positioned either side of said support foot 46; Such an embodiment is illustrated in a non-limiting manner in FIGS. 2 to 4. In such a case, the foot 46 is positioned at the mid-distance between the sensors, which are then positioned on either side of the flexible guide 3 on which the sensor support 41 is rigidly attached. Such ("double") sensor supports will be particularly useful for positioning sensors on areas of the cranium having strong curvature.

Figure 7:
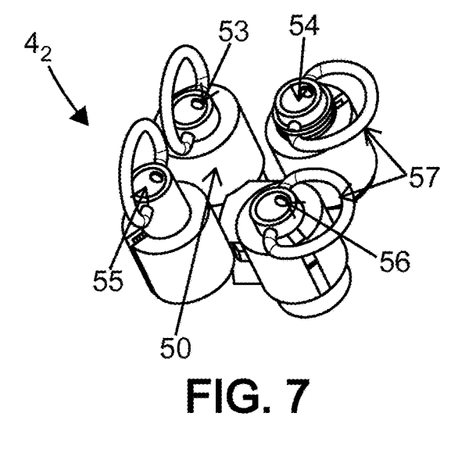
FIGS. 7, 8 and 9 are respectively a perspective view, a view from above, and a sectional view along section VIII-VIII of FIG. 8, of a sensor support having four sensors.
Figure 8:
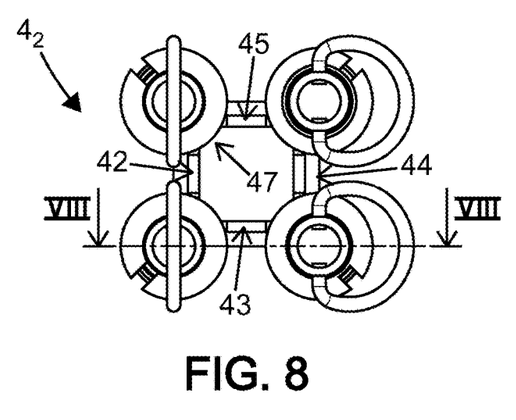
Figure 9:
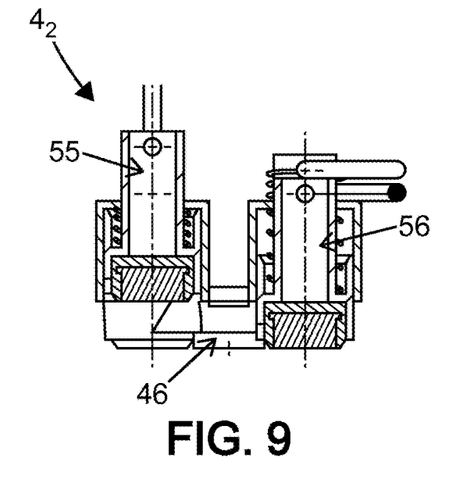

The so-called multiple sensor supports can comprise ("quadruple") sensor supports $4_2$ for four sensors, intended to be distributed around said support foot 46. The four sensors can be positioned at the four vertices of a rectangle (for example a square). Such an embodiment is illustrated in a non-limiting manner in FIGS. 7 to 8. Such an embodiment is particularly interesting in that it enables grouping of four sensors clustered about a given area of interest of the cranium, but needs however to be applied on a relatively flat area of the cranium.

Hence, and as illustrated in FIG. 1, the ("double") sensor supports and the ("quadruple") sensor supports can be combined on the structure. It is well understood that FIG. 1 is a partial figure, in that it only illustrates some of the sensor supports, the others not being illustrated for reasons of clarity, in order to render the structure visible, in particular the various flexible guides 3.

According to an advantageous embodiment, each sensor is intended to be moveably mounted, by sliding, with respect to the portion of the sensor support equipped with the support foot 46; a spring element 48, such as a compression spring, being configured to constrain the sensor in the direction towards and pressing on the head of the wearer.

Advantageously, one such embodiment makes it possible to ensure that the or each sensor is correctly positioned pressing on the head of the individual, while controlling the pressing force of said sensor on the head.

To this effect, the spring element 48, in particular the compression spring, is selected such that the recall force is sufficient to press the sensor onto the head, but has sufficiently low stiffness so that the force is not painful. In the case of a multiple sensor support, each sensor can move relative to the support portion equipped with the foot 46, independently of the other sensors. Each sensor has an independent spring element 48. As shown in a non-limiting manner in FIG. 4 (right-hand side), the course of the sensor is such that at the high end of the course, it is raised substantially above the level of the support foot 46. In other words, when the sensor is at a level corresponding to the bearing surface of the foot as illustrated in a non-limiting manner in FIG. 4 (left-hand side), or in the vicinity thereof, the force of the sensor on the head is limited by the choice of the spring element 48, and in particular by the choice of the stiffness thereof and the rate of compression thereof at this position (the pretensioning). By way of non-limiting example, the spring element 48 may have a stiffness of 40 N/m, the pretensioning being defined at 0.25 N when the lower end of the sensor is at the same level as the bearing surface of the foot 46. The structure of the device allows distribution of the loads reducing the point pressure areas.

According to one embodiment, said sensor support portion equipped with said bearing support foot 46 being termed the fixed part 49; 50, said sensor support $4_1$, $4_2$ comprises, for the or each sensor, a moveable part 51, 52; 53, 54; 55, 56 movable with respect to said fixed part, rigidly attached to the sensor, said spring element 48 being provided between the fixed part and the movable part of the sensor support.

To this effect and according to an illustrated embodiment, the fixed part 49; 50 comprises, for the or each sensor, a hollow shaping, in particular cylindrical, inside of which said movable part is intended to slide. Said movable part of the sensor support has a lower terminal end, for the attachment of a sensor, as well as a guide surface, in particular cylindrical, intended to slide along the inner wall of the hollow shaping.

Figure 5:
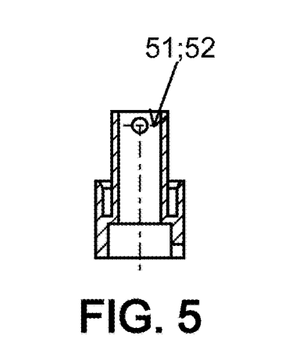
FIG. 5 is a sectional view of the movable section of the sensor support, according to an embodiment of the invention, and suitable for a type of sensor, in particular an electrode.
Figure 6A:
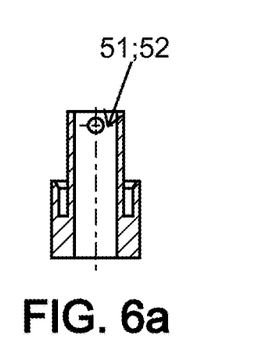
FIG. 6a is a cross-sectional view of the movable part of the sensor support, according to an embodiment of the invention, and suitable for a type of sensor, in particular an optode transmitter.
Figure 6B:
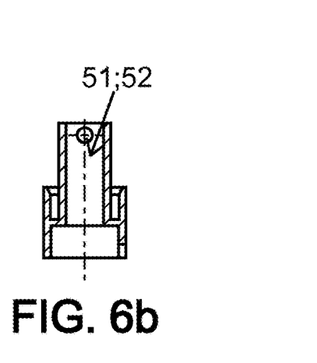
FIG. 6b is a cross-sectional view of the movable part of the sensor support, according to an embodiment of the invention, and suitable for a type of sensor, in particular an optode detector.

As illustrated in FIGS. 5 and 6a and 6b in particular, the movable part 51 or 52 of the sensor support can be specific to a particular sensor type, thus playing the role of an adapter. The device may thus comprise a set of movable parts, respectively constituting different adapters for the installation of different physically distinct sensors, such as electrodes, or the transmitter or detector of an optode. For example, the moveable part of the support illustrated in FIG. 5 is an adapter suitable for the attachment of an electrode, whereas the moveable parts of FIG. 6a and FIG. 6b respectively enable the installation of the transmitting and detecting part of an optode.

According to one embodiment, said movable part has a projecting portion extending through an upper opening of the hollow shaping, a locking member 57, such as a pin, being mounted in a removable manner on the projecting portion, in such a way as to both ensure the retention and locking of said moveable part 51, 52; 53, 54, 55, 56 to said fixed part 49; 50 of the sensor support $4_1$, $4_2$, as well as to enable, once the locking member is withdrawn, the withdrawal and dismantling of the moveable part 51, 52; 53, 54, 55, 56 from the fixed part 49; 50. The assembly and disassembly of the locking member 57 are preferably carried out without a tool.

The locking member 57 may advantageously take the shape of a loop, intended for gripping, and allowing the sensor to be removed from the surface of the head when a traction force is applied on the loop. The loop is an elastically deformable element, for example a metal element, having two free ends intended to be inserted in the corresponding holes of the projecting portion.

Figure 4:
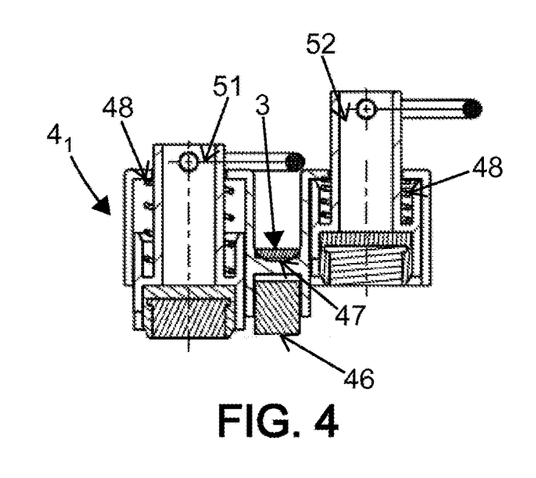

As illustrated on the left hand side of FIG. 4, said locking member 57, once installed, abuts the fixed part at the lower end of the course, preventing withdrawal of the movable part from the hollow shaping of the fixed part. The loop is withdrawn by deforming same, so as to remove the free ends from the holes. Once the loop is withdrawn, the movable part can be extracted from the hollow shaping.

The body of the fixed part of the sensor may be a plastic part, in particular an injection moulded part, with the feet consisting of an elastomer element attached to the body. Similarly, each moveable part 51, 52; 53, 54, 55, 56 may be a plastic element, in particular injection moulded.

Figure 10:
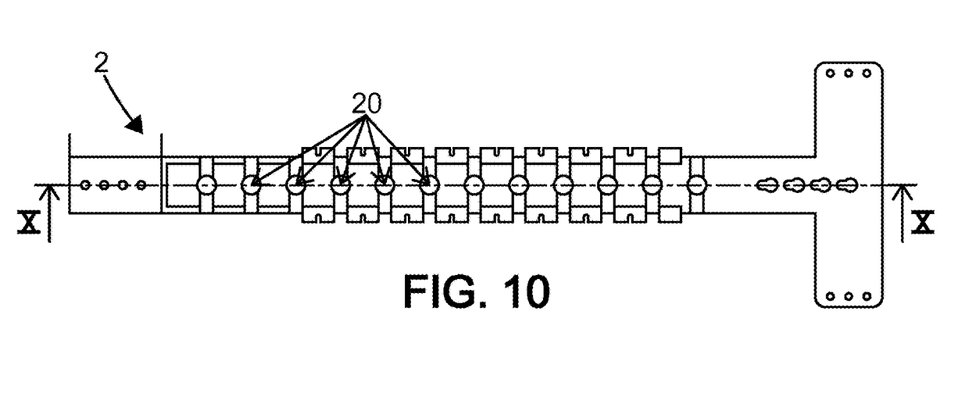
FIGS. 10, 11 and 12, are respectively a view from above, a sectional view along section X-X of FIG. 10, and a front view, of a central support according to an example.
Figure 11:
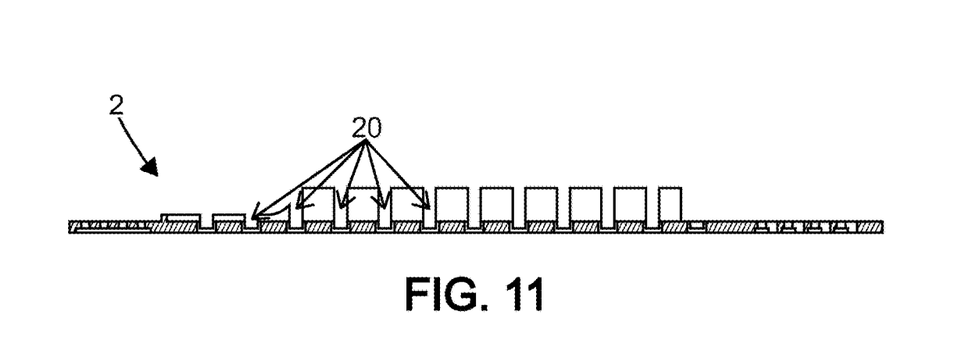
Figure 12:
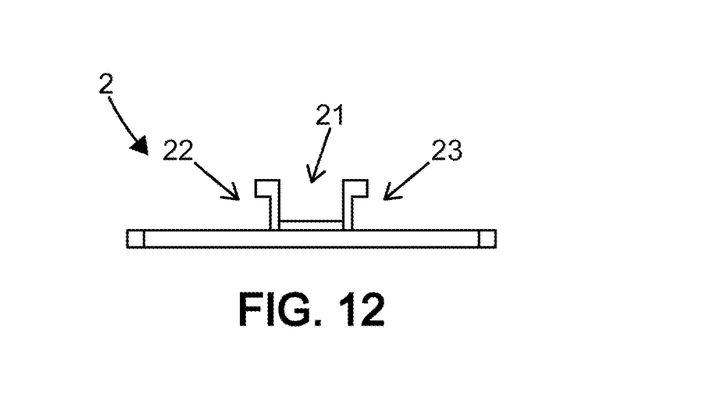

The central support 2 can comprise a plurality of through-passages 20 in the longitudinal direction, in particular in the form of the grooves, mutually spaced along the length of said central support for the respective positioning and retaining of a plurality of flexible guides 3, having different separated positions defined between said flexible guides.

Said central support 2 can comprise a longitudinal channel 2 following the longitudinal direction, functioning as a cable guide intended for guiding the wiring connections of the various sensors. The central support 2 may be an elastomer element which comprises a central band, the lower surface of which is intended to bear on the head, and the upper surface being provided with said through-passages, with large depth and in the form of grooves respectively distributed along the band. Said central support can present discontinuous raised edges 22, 23, between the grooves, along the two longitudinal edges of the band and forming, with said central band, the longitudinal channel 21. The central support 2 can be made from an elastomer material and obtained, in particular, by moulding.

Figure 15:
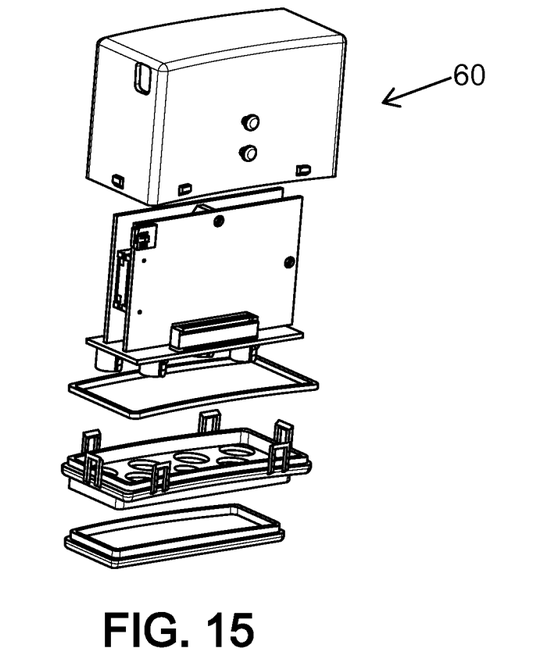
FIG. 15 is an exploded view of an enclosure, the cover thereof and an electronics card for acquisition of measurement signals.

The channel 21 can be used to guide the wiring connections of the sensors towards an enclosure accommodating electronics for acquisition of sensor signals, said enclosure being rigidly attached to the structure and positioned at the rear part of the head. Said enclosure internally houses electronics for acquiring measurement signals, in particular signals from near-infrared spectroscopy and/or signals from electroencephalography. In the case of the use of near-infrared spectroscopy, the device can also comprise a removable cover (not illustrated), made from an obscuring material, intended to be applied on the structure of the sensor support of the device, in such a way as to isolate the sensors (in particular the optodes) from optical interference from the ambient environment. Such a cover advantageously allows a wearer to carry out NIRS measurements in compliance with the recording conditions (i.e. in the dark), and without requiring the wearer to be in the dark. The cover can be made from a lightweight obscuring material, in order not to bear on the sensor supports, and having a tightening link and/or an elastic piece on the rim thereof, in order to be able to adjust the cover to different head sizes.

REFERENCE SIGNS 1. device
2. central support
3. flexible guides
4$_1$, 4$_2$. sensor supports (with two sensors or four sensors respectively)
5. elastic pieces
6. braces
7. through-openings (braces 6)
20. through-passages (central support 2)
21. longitudinal channel (central support 2)
22, 23. raised edges (central support 2)
40, 41. feedthroughs (sensor supports 41)
42, 43, 44, 45. feedthroughs (sensor supports 42)
46. foot (sensor support 41 or 42)
47. dorsal surface
48. spring element (compression spring for example)
49. fixed part (sensor supports 4$_1$)
50. fixed part (sensor supports 4$_2$)
51, 52. movable parts (sensor supports 4$_1$)
53, 54, 55, 56. movable parts (sensor supports 4$_2$)
57. locking member (in particular gripping loop)
60. enclosure (acquisition electronics)
61. chinstrap

The invention claimed is:

1. A device for measuring brain activity signals of an individual, said device being configured to be placed on the head of said individual, to carry a plurality of sensors, and to enable positions of the sensors to be adjusted, said device comprising:
a deformable central support configured to adapt to a curvature of the head and to be positioned along the head;
a plurality of flexible guides extending laterally with respect to said central support and spaced apart from one another;
a plurality of sensor supports rigidly connected and fixed to said flexible guides, the sensor supports being in adjustable positions along the flexible guides, the sensor supports having feedthroughs configured to receive the flexible guides to allow position adjustment, all or part of the plurality of sensor supports being multiple sensor supports, each of the multiple sensor supports supporting at least two physically distinct sensors of the plurality of sensors, the at least two physically distinct sensors being of different types,
each of the sensor supports comprising a portion having a support foot configured to bear on the head of the wearer, in a central position with respect to the positions of the supported sensors, the portion of the sensor support having the support foot comprising
the feedthroughs, crossed by one of the flexible guides, and a dorsal surface on which a longitudinal section of the respective flexible guide bears, the sensors being disposed on either side of the flexible guide bearing on the dorsal surface, the dorsal surface being disposed just above the foot; and
a tension system configured to tension said flexible guides.

2. The device according to claim 1, said tension system comprises, on each side of the head of the wearer,
a rigid brace configured to extend at least locally under an ear of the individual, and
a plurality of elastic pieces, each of the elastic pieces being rigidly attached by one of the ends thereof to a lower terminal end below the corresponding flexible guide, each of the elastic pieces being configured to be attached to said brace in order to ensure tensioning of the corresponding flexible guide.

3. The device according to claim 2, wherein said tension system comprises at least one tension adjustment system configured to adjust the tension of the elastic pieces.

4. The device according to claim 3, wherein the at least one tension adjustment system comprises a through-opening of the brace for the respective elastic piece, said through-opening having dimensions less than a cross-section of the respective elastic piece, such that:
a manual pulling force on a free end of the elastic piece causes the elastic piece to slide through said through-opening, and thus enables adjustment by increasing the tension, and
when the manual pulling force is no longer applied, frictional forces between the through-opening and the elastic piece occur to prevent sliding, ensuring tensioning of the corresponding flexible guide.

5. The device according to claim 1, wherein the flexible guides are an inelastic material.

6. The device according to claim 5, wherein the flexible guides are a textile.

7. The device according to claim 1, wherein said flexible guides are bands.

8. The device according to claim 1, wherein, after a manual adjustment operation has been carried out, the respective sensor support is held in position on the respective flexible guide by frictional forces between the flexible guide and the sensor support.

9. The device according to claim 1, wherein said portion of the sensor support having the support foot comprises
two of the feedthroughs that are respectively disposed on either side of said foot, both of the two feedthroughs being crossed by one of the flexible guides, and
the dorsal surface on which the longitudinal section of said flexible guide bears at a position intermediate between the two feedthroughs.

10. The device according to claim 1, wherein said multiple sensor supports comprise a set of the sensor supports for two of the sensors configured to be positioned on either side of said support foot.

11. The device according to claim 1, wherein said multiple sensor supports comprise a set of the sensor supports for four of the sensors configured to be positioned around said support foot.

12. The device according to claim 1, wherein each of the sensors is configured to be moveably mounted, by sliding, with respect to the portion of the sensor support equipped with the support foot, a spring element being configured to compel the respective sensor in the direction towards and bearing on the head of the individual.

13. The device according to claim 12, wherein said sensor support portion equipped with said bearing support foot is a fixed part, said sensor support including, for at least one of the sensors, a moveable part movable with respect to said fixed part rigidly attached to the at least one sensor, said spring element being provided between the fixed part and the moveable part of the sensor support.

14. The device according to claim 13, wherein said fixed part comprises, for the at least one sensor, a hollow shaping that is cylindrical, the movable part being configured to slide inside of the hollow shaping, and
   said movable part of the sensor support has a terminal end configured to attach to one of the sensors, and a guide surface configured to slide along an inner wall of the hollow shaping.

15. The device according to claim 14, wherein the movable part has a projecting portion extending through an upper opening of the hollow shaping, a locking member being removably mounted on the projecting portion to both ensure retention and locking of said moveable part to said fixed part of the sensor support and to enable withdrawal and dismantling of the moveable part from the fixed part when the locking member is withdrawn.

16. The device according to claim 15, wherein the locking member is a loop configured to grip and to allow the respective sensor to be removed from a surface of the head when a traction force is applied on the loop.

17. The device according to claim 1, wherein said central support has, in the longitudinal direction, a plurality of through passages, mutually spaced along a length of said central support for the respective positioning and retaining of the plurality of flexible guides, having different separated positions defined between said flexible guides.

18. The device according to claim 1, wherein said central support forms, along a longitudinal direction, a longitudinal canal acting as a cable guide, the longitudinal canal being configured to guide wiring connections of the sensors.

19. The device according to claim 1, further comprising an enclosure accommodating electronics for acquisition of sensor signals.

20. The device according to claim 1, wherein the sensors comprise at least one of (i) electrodes configured to measure signals by electroencephalography and (ii) optical detectors and transmitters configured to measure signals by near-infrared spectroscopy.

21. The device according to claim 1, further comprising a removable cover, made from an obscuring material, the removable cover being configured to be applied on the sensor support to isolate the sensors from optical interference from the ambient environment.

22. A method for measuring signals by electroencephalography, comprising:
   providing the device of claim 20 equipped with sensors comprising electrodes; and
   using said optical detectors and transmitters for measuring signals by a near-infrared spectroscopy, for simultaneously measuring said signals by electroencephalography and near-infrared spectroscopy.

* * * * *